US012778128B2

(12) United States Patent
Osei-Owusu et al.

(10) Patent No.: US 12,778,128 B2
(45) Date of Patent: Nov. 3, 2026

(54) ANTI-MICROBIAL COMPOSITION AND METHOD OF USING SAME

(71) Applicant: ARXADA, LLC, Morristown, NJ (US)

(72) Inventors: Luke Osei-Owusu, Bronx, NY (US); Xiao Jiang, Montvale, NJ (US); Marcus Bentley, Monroe Township, NJ (US)

(73) Assignee: Arxada, LLC, Morristown, NJ (US)

( * ) Notice: Subject to any disclaimer, the term of this patent is extended or adjusted under 35 U.S.C. 154(b) by 755 days.

(21) Appl. No.: 17/626,176

(22) PCT Filed: Jul. 1, 2020

(86) PCT No.: PCT/US2020/040505
§ 371 (c)(1),
(2) Date: Jan. 11, 2022

(87) PCT Pub. No.: WO2021/011197
PCT Pub. Date: Jan. 21, 2021

(65) Prior Publication Data
US 2023/0255209 A1 Aug. 17, 2023

Related U.S. Application Data

(60) Provisional application No. 62/873,629, filed on Jul. 12, 2019.

(51) Int. Cl.

| | |
|---|---|
| ***A01N 59/00*** | (2006.01) |
| ***A01N 37/02*** | (2006.01) |
| ***A01N 37/04*** | (2006.01) |
| ***A01N 37/36*** | (2006.01) |
| ***A01P 1/00*** | (2006.01) |
| ***A61L 2/186*** | (2026.01) |

(52) U.S. Cl.
CPC ............. *A01N 59/00* (2013.01); *A01N 37/02* (2013.01); *A01N 37/04* (2013.01); *A01N 37/36* (2013.01); *A01P 1/00* (2021.08); *A61L 2/186* (2013.01)

(58) Field of Classification Search
None
See application file for complete search history.

(56) References Cited

U.S. PATENT DOCUMENTS

| | | | | |
|---|---|---|---|---|
| 6,627,667 | B2 † | 9/2003 | Hllgren | |
| 10,064,409 | B2 | 9/2018 | Hazenkamp et al. | |
| 11,167,054 | B2 | 11/2021 | Lei et al. | |
| 2002/0016278 | A1 † | 2/2002 | Barbeau | |
| 2008/0010772 | A1 | 1/2008 | Kong et al. | |
| 2009/0221704 | A1 * | 9/2009 | Aksela | C07C 409/30 514/557 |
| 2011/0182958 | A1 * | 7/2011 | Omidbakhsh | A01N 25/30 424/405 |
| 2012/0171155 | A1 † | 7/2012 | Cunningham | |
| 2016/0176814 | A1 * | 6/2016 | Balasubramanian | C07C 409/24 562/6 |
| 2017/0081618 | A1 * | 3/2017 | Gohl | C11D 3/2075 |
| 2017/0275472 | A1 | 9/2017 | Yeung et al. | |
| 2019/0281823 | A1 * | 9/2019 | Bolduc | A61L 2/186 |
| 2020/0157046 | A1 | 5/2020 | Balasubramanian et al. | |

FOREIGN PATENT DOCUMENTS

| | | |
|---|---|---|
| EP | 0231632 | 8/1987 |
| WO | WO9420424 | 9/1994 |
| WO | WO2019103887 | 5/2019 |

OTHER PUBLICATIONS

Chinese Office Action for CN202080059555.7 dated Apr. 29, 2023, 28 pages.
International Search Report for PCT/US2020/040505 dated Sep. 21, 2020, 13 pages.
Anonymous: "Methanesulfonic Acid 175-75-21 B2B Partner I Vivochem-Vivochem.en", pp. 1-4, https://www.vivochem.com/en/p/methanesulfonic-acid.
Australian Examination Report for EP2020315254 dated Jun. 29, 2026, 4 pages.

* cited by examiner
† cited by third party

*Primary Examiner* — H. Sarah Park
(74) *Attorney, Agent, or Firm* — Dority & Manning, P.A.

(57) ABSTRACT

An antimicrobial composition contains hydrogen peroxide, an organic sulfonic acid, and a peroxide adjuvant. The peroxide adjuvant is a small molecule organic acid, such as formic acid. The antimicrobial composition is very effective at sanitizing surfaces in all different types of fields, such as in the healthcare industry. The antimicrobial composition is well suited for controlling *C. difficile*.

10 Claims, 1 Drawing Sheet

ANTI-MICROBIAL COMPOSITION AND METHOD OF USING SAME

RELATED APPLICATIONS

The present application is the National Stage entry of International Patent Application No. PCT/US2020/040505, filed on Jul. 1, 2020, which is based on and claims priority to US Provisional Patent Application Ser. No. 62/873,629, filed on Jul. 12, 2019, which are incorporated herein by reference.

BACKGROUND

Antimicrobial compositions are used in numerous and diverse applications. In general, antimicrobial compositions are used to destroy microorganisms and/or prevent the growth of microorganisms. Antimicrobial compositions are used, for instance, to disinfect or sanitize objects in the food service industry, in the healthcare industry, in industrial settings, and for consumer household use. In one embodiment, antimicrobial compositions are used to sanitize or disinfect surfaces, such as hard, non-porous surfaces.

Some antimicrobial compositions are known to contain hydrogen peroxide. Hydrogen peroxide has advantages and benefits to being used as a disinfectant and biocide because it decomposes to oxygen and water and therefore is very safe to use. Another advantage to hydrogen peroxide is that it has a broad spectrum of biocidal activities against many different types of organisms. Unfortunately, however, hydrogen peroxide, when used alone, can have a relatively low rate of activity.

In view of the above, those skilled in the art have attempted to produce antimicrobial solutions containing hydrogen peroxide that have enhanced biocide properties. In particular, those skilled in the art have attempted to produce hydrogen peroxide solutions with improved efficacy and killing rate against a variety of microorganisms. In this regard, in the past, hydrogen peroxide has been combined with various other chemical species in order to improve efficacy against various microorganisms. For example, in the past, hydrogen peroxide has been combined with acetic acid and/or peracetic acid. Although adding acetic acid and/or peracetic acid with hydrogen peroxide can increase the effectiveness of the antimicrobial composition, the resulting composition has a very unpleasant, pungent odor.

One particular microorganism that is difficult to control using hydrogen peroxide compositions is *Clostridium difficile. C. difficile* is a pathogen that is capable of causing severe gastrointestinal disease in mammals, especially humans. In fact, *C. difficile* is the leading cause of hospital-acquired diarrhea and is the primary cause of pseudomembranous colitis. The number of cases of *C. difficile* associated diseases has continued to increase annually. For instance, patients that are on antibiotics or undergoing chemotherapy are particularly susceptible to acquiring a *C. difficile* associated disease. As the frequency of disease has increased, hospitals have become even more contaminated with spores of *C. difficile* making infection of susceptible patients more probable.

In view of the above, a need currently exists for an antimicrobial composition containing hydrogen peroxide that has increased efficacy against microorganisms without having an unpleasant odor. A need also exists for a hydrogen peroxide-based antimicrobial composition that is effective against the microorganism, *Clostridium* difficile.

SUMMARY

The present disclosure is generally directed to an antimicrobial composition that is effective against a broad range of microorganisms, including *Clostridium difficile*. Not only is the antimicrobial composition of the present disclosure safe and non-hazardous, but the composition is also efficacious against a broad range of microorganisms even when diluted to very low concentrations. The antimicrobial composition can be formulated to be free of acetic acid and/or peracetic acid and thus does not have an unpleasant odor associated with use of the composition.

In general, the antimicrobial composition of the present disclosure contains a peroxide source, such as hydrogen peroxide. In accordance with the present disclosure, the peroxide source is combined with an organic sulfonic acid and a peroxide adjuvant. The peroxide adjuvant comprises an organic acid having a pKa of greater than about 1, such as greater than about 2, such as greater than about 3, and generally less than about 6, such as less than about 5, such as less than about 4. In one embodiment, the peroxide adjuvant comprises a low molecular weight organic acid and/or salt thereof. In accordance with the present disclosure, the peroxide adjuvant is present in the antimicrobial composition in an amount sufficient for the composition to achieve at least a 3 $\log_{10}$ reduction after a three minute contact time when tested against *Clostridium difficile* according to ASTM Test Methods ASTM E2197-11 and E2839-11. For instance, the composition of the present disclosure can achieve at least a 4 $\log_{10}$ reduction, such as at least a 5 $\log_{10}$ reduction, such as at least a 6 $\log_{10}$ reduction after a 3 minute contact time.

In one aspect, the peroxide adjuvant is an organic acid or salt thereof containing only one or two carbon atoms. For instance, the peroxide adjuvant can be formic acid, a formic acid salt, or mixtures thereof. Alternatively, the peroxide adjuvant can comprise glycolic acid, a salt of glycolic acid, or mixtures thereof. In one embodiment, the composition contains both formic acid and/or a salt of formic acid and glycolic acid and/or a salt of glycolic acid.

The organic sulfonic acid can be a non-surfactant sulfonic acid. For example, the organic sulfonic acid can be a $C_1$-$C_7$ alkylsulfonic acid, a sulfonated $C_1$-$C_7$ carboxylic acid, a substituted or unsubstituted aromatic sulfonic acid, mixtures thereof and salts thereof. In another embodiment, the alkylsulfonic acid and sulfonated carboxylic acid have a $C_1$-$C_5$ chain. In the case of a substituted aromatic sulfonic acid, the aromatic ring can be substituted with at least one $C_1$-$C_3$ alkyl group, Stated otherwise, if the aromatic ring is substituted, the alkyl group may contain three (3) carbons or less. Salts of the non-surfactant organic sulfonic acid are alkali metal and alkaline earth metals salts, such as sodium, potassium, calcium and magnesium. Salts may also include ammonium salts. Representative examples of the non-surfactant organic sulfonic acid are methane sulfonic acid, benzene sulfonic acid, toluene sulfonic acid, xylenesulfonic acid, ethylbenzene sulfonic acid, and mixtures thereof.

Examples of organic sulfonic acids that may be used include methane sulfonic acid, benzene sulfonic acid, toluene sulfonic acid, xylene sulfonic acid, ethylbenzene sulfonic acid and mixtures thereof.

In one aspect, the weight ratio between the hydrogen peroxide and the peroxide adjuvant is from about 100:1 to about 1:2, such as from about 20:1 to about 1:1, such as from about 8:1 to about 2:1. The weight ratio between the hydrogen peroxide and the organic sulfonic acid, on the other hand, can be from about 100:1 to about 1:3, such as from about 10:1 to about 1:1.1, such as from about 3:1 to about 1:0.9.

The hydrogen peroxide source (or hydrogen peroxide) can generally be present in the composition in an amount of from about 0.2% to about 20% by weight, such as from about 1% to about 15% by weight, such as from about 1% to about 8% by weight, such as from about 2% to about 6% by weight. The organic sulfonic acid can be present in the composition generally in an amount from about 0.1% to 8% by weight, such as from about 0.5% to about 6% by weight, such from about 1% A to about 5% by weight. The peroxide adjuvant, on the other hand, can generally be present in the antimicrobial composition in an amount from about 0.05% to about 7% by weight, such as from about 0.08% to about 5% by weight, such as from about 0.1% to about 4% by weight.

The antimicrobial composition generally comprises a liquid medium having a pH of less than about 6, such as less than about 5, such as less than about 4, such as less than about 3, such as less than about 2. The pH is generally greater than about 0.5, such as greater than about 1, such as greater than about 1.25. The composition can also contain a liquid carrier. The liquid carrier may comprise water, an alcohol, or mixtures thereof.

The present disclosure is also directed to an antimicrobial composition precursor. The precursor is formulated for later combining with a hydrogen peroxide source. The antimicrobial composition precursor can comprise an organic sulfonic acid generally present in an amount from about 15% to about 60% by weight combined with a peroxide adjuvant as described above. The peroxide adjuvant can be present in the composition in an amount from about 5% to about 20% by weight. The composition can further contain sodium hydroxide in an amount from about 3% to about 20% by weight, such as in an amount from about 8% to about 15% by weight. The remainder of the composition can water and hydroxyethylidene 1,1 diphosphonic acid.

The present disclosure is also directed to a method for disinfecting a hard or soft surface. The method includes the step of contacting a surface with an antimicrobial composition as described above. The hard surface can be a surface used in the health care industry or in a veterinarian industry. Alternatively, the hard surface can comprise food processing equipment or a food preparation service.

The antimicrobial composition of the present disclosure can be applied to surfaces using various different techniques. For instance, the composition can be sprayed or otherwise applied to a surface directly. Alternatively, the antimicrobial composition can be applied to a wiping product which is then used to apply the composition to a surface. In this regard, the present disclosure is also directed to a premoistened wiping product containing the antimicrobial composition as described above.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
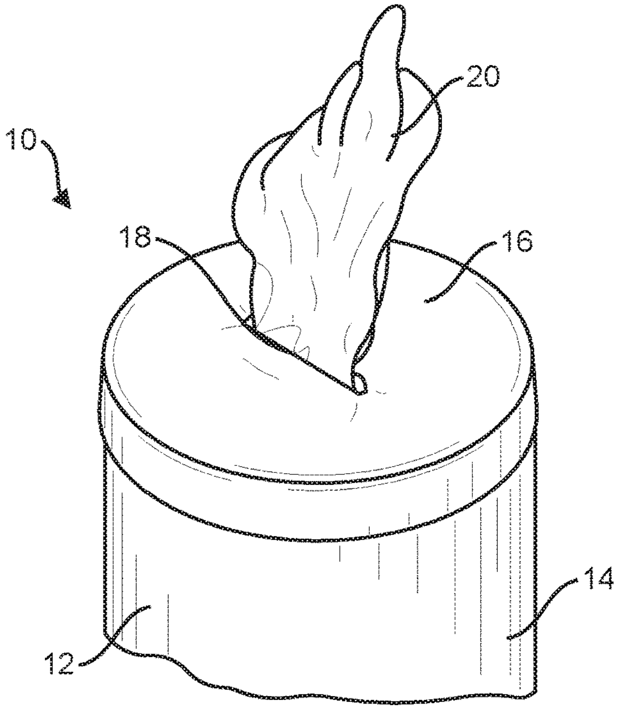
FIG. 1 is a perspective view with cutaway portions of one embodiment of a wiping product made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to an antimicrobial composition that contains a hydrogen peroxide source in combination with an organic sulfonic acid and a peroxide adjuvant. The peroxide adjuvant is an organic acid and/or a salt thereof, and particularly a low molecular weight organic acid and/or salt thereof. The presence of the peroxide adjuvant in combination with the organic sulfonic acid dramatically improves the antimicrobial properties of the composition, especially when compared to a composition only containing hydrogen peroxide or a composition containing hydrogen peroxide and an acetic acid. It was discovered that the combination of a hydrogen peroxide source with an organic sulfonic acid and a peroxide adjuvant significantly enhances antimicrobial activity against a broad range of microorganisms. More particularly, it was discovered that the antimicrobial composition of the present disclosure is particularly well suited to destroying and inhibiting the growth of *Clostridium difficile* even when contact times are relatively short. For example, the antimicrobial composition of the present disclosure is capable of achieving at least a 3 $\log_{10}$ reduction against *C. difficile* when tested according to ASTM Test Methods ASTM E2197-11 and E2839-11 and after a 3 minute contact time. The antimicrobial composition of the present disclosure is also capable of achieving at least a 4 $\log_{10}$ reduction, such as at least a 5 $\log_{10}$ reduction, such as at least a 6 $\log_{10}$ reduction against *C. difficile* after a 3 minute contact time.

Although unknown, it is believed that the small organic acid molecule and the organic sulfonic acid create a unique combination that activates the efficacy of hydrogen peroxide. Of particular advantage, the antimicrobial composition of the present disclosure has dramatically lower odor properties compared to many conventional products. For instance, the antimicrobial composition of the present disclosure can be formulated so as to be free of acetic acid, free of peracetic acid, and/or free of chlorine bleach. The three primary components contained in the antimicrobial composition have shown synergistic efficacy against various different microorganisms, including *C. difficile.*

The antimicrobial composition of the present disclosure can be used in numerous and diverse applications. In one embodiment, for instance, the antimicrobial composition may be used to sanitize or disinfect hard, non-porous surfaces. For example, the antimicrobial composition is well suited for disinfecting or sanitizing flooring materials, countertops, ceramic surfaces, metal surfaces, glass surfaces, stone surfaces, and the like.

The antimicrobial composition is also well suited to sanitizing soft surfaces. Examples of soft surfaces include, but are not limited to, upholstery, fabric, upholstered couches, sofas, chairs, seat cushions, upholstered cushions, pillows, upholstered furniture, fabric window treatments, curtains, draperies, shower curtains, fabric gym/laundry diaper bags, backpacks, fabric hampers, fabric dog/pet bedding, blankets, fabric upholstered car seats, fabric stuffed animals, toys, and the like.

The antimicrobial composition can be used to clean the surfaces, destroy microorganisms on the surface and/or prevent growth of microorganisms on the surface. The antimicrobial composition can be used in numerous different fields. For instance, the antimicrobial composition is well suited for use in the healthcare industry to disinfect surfaces and/or disinfect utensils. The antimicrobial composition can be used in hospitals, for example, in order to prevent the spread of *C. difficile*. The antimicrobial composition can be used in the food service industry to disinfect and sanitize food processing equipment and other food processing surfaces or to wash produce, such as vegetables. The antimicrobial composition can also be sold for consumer household use. The composition can be used in a concentrated or diluted form depending upon the application.

The antimicrobial composition generally contains a peroxide source in combination with an organic sulfonic acid and a peroxide adjuvant. The peroxide source may comprise hydrogen peroxide. In other embodiments, however, the peroxide source may comprise a compound that produces hydrogen peroxide. Hydrogen peroxide sources can include, for instance, solutions of alkali-metal hydrogen peroxides, alkali salts of percarbonate and persulfate, and organic peroxides. Organic peroxides can include dicumyl peroxide, dialkyl peroxides, urea peroxides, and the like. Hydrogen peroxide itself can provide numerous advantages and benefits. Hydrogen peroxide not only has activity against a broad range of microorganisms but is also relatively safe to use. Hydrogen peroxide can oxidize and/or bleach a surface, while degrading into very safe byproducts, namely oxygen and water.

The amount of hydrogen peroxide contained in the composition can depend on numerous factors including the ultimate end use application. Hydrogen peroxide can be added to the composition in order to generate one or more peroxyacids. In general, hydrogen peroxide can be added in excess such that it remains in the composition after a reaction equilibrium has been reached with respect to the other components. In one aspect, the antimicrobial composition can contain the hydrogen peroxide source generally in an amount of from about 0.2% by weight to about 20% by weight, including all increments of 0.1% by weight therebetween. For example, the hydrogen peroxide source can be present in the antimicrobial composition in an amount greater than about 0.5% by weight, such as in an amount greater than about 1% by weight, such as in an amount greater than about 1.5% by weight, such as in an amount greater than about 2% by weight, such as in an amount greater than about 2.5% by weight, such as in an amount greater than about 3% by weight. The hydrogen peroxide source can generally be present in an amount less than about 15% by weight, such as in an amount less than about 10% by weight, such as in an amount less than about 8% by weight, such as in an amount less than about 6% by weight.

In accordance with the present disclosure, the antimicrobial composition also contains an organic sulfonic acid. The organic sulfonic acid can be a non-surfactant sulfonic acid. Examples of sulfonic acids that may be used include $C_1$-$C_7$ alkylsulfonic acid, a sulfonated $C_1$-$C_7$ carboxylic acid, a substituted or unsubstituted aromatic sulfonic acid, mixtures thereof and salts thereof. In another embodiment, the alkylsulfonic acid and sulfonated carboxylic acid have a $C_1$-$C_5$ chain. In the case of a substituted aromatic sulfonic acid, the aromatic ring can be substituted with at least one $C_1$-$C_3$ alkyl group. Stated otherwise, if the aromatic ring is substituted, the alkyl group can contain three (3) carbons or less. Salts of the non-surfactant organic sulfonic acid are alkali metal and alkaline earth metals salts, such as sodium, potassium, calcium and magnesium. Salts may also include ammonium salts. Representative examples of the non-surfactant organic sulfonic acid are methane sulfonic acid, benzene sulfonic acid, toluene sulfonic acid, xylenesulfonic acid, ethylbenzene sulfonic acid, and mixtures thereof.

The organic sulfonic acid can generally be present in the antimicrobial composition in an amount of from about 0.1% by weight to about 10% by weight including all increments of 0.1% by weight therebetween. For example, the organic sulfonic acid can be present in the antimicrobial composition in an amount greater than about 0.5% by weight, such as in an amount greater than about 1% by weight, such as in an amount greater than about 1.5% by weight, such as in an amount greater than about 2% by weight and generally in an amount less than about 8% by weight, such as in an amount less than about 6% by weight, such as in an amount less than about 5% by weight.

The antimicrobial composition of the present disclosure further contains a peroxide adjuvant. In one aspect, the peroxide adjuvant is an organic acid having a pKa of less than about 6, such as less than about 5, such as less than about 4, such as less than about 3, such as less than about 2. The pKa of the organic acid can generally be greater than about 1, such as greater than about 2, such as greater than about 3, such as greater than about 4. In one aspect, the peroxide adjuvant comprises a low molecular weight organic acid and/or salt thereof. The organic acid or salt thereof, for example, may contain about 10 carbon atoms or less per molecule, such as less than about 8 carbon atoms, such as less than about 6 carbon atoms, such as less than about 4 carbon atoms, such as less than about 3 carbon atoms. In one aspect, the peroxide adjuvant may comprise a carboxylic acid having only a single carbon atom, such as formic acid and/or carbonic acid. In other embodiments, the organic acid can comprise a bicarboxylic acid, such as oxalic acid. In still another aspect, the organic acid can be a tricarboxylic acid, such as citric acid. Alternatively, the peroxide adjuvant may comprise an alpha hydroxy acid having less than 3 carbon atoms, and may comprise glycolic acid or a salt thereof. The peroxide adjuvant may also comprise a mixture of any of the above described organic acids.

Only very minor amounts of the peroxide adjuvant need to be present in the antimicrobial composition for synergistic results to occur. For instance, the peroxide adjuvant can be present in the antimicrobial composition generally in an amount of from about 0.05% by weight to about 10% by weight including all increments of 0.1% by weight therebetween. In one aspect, the peroxide adjuvant is present in the antimicrobial composition in an amount greater than about 0.08% by weight, such as in an amount greater than about 0.1% by weight, such as in an amount greater than 0.2% by weight, such as in an amount greater than 0.5% by weight, such as in an amount greater than 0.8% by weight, such as in an amount greater than 1% by weight. The peroxide adjuvant is generally present in an amount less than about 7% by weight, such as in an amount less than about 5% by weight, such as in an amount less than about 4% by weight.

The weight ratio between the hydrogen peroxide source and the organic sulfonic acid and the weight ratio between the hydrogen peroxide source and the peroxide adjuvant can vary depending upon the particular application and the desired result. In one aspect, the weight ratio between the hydrogen peroxide source and the organic sulfonic acid can be from about 100:1 to about 1:3, such as from about 10:1 to about 1:1.1, such as from about 3:1 to about 1:0.9. The weight ratio between the hydrogen peroxide source and the peroxide adjuvant, on the other hand, is generally from about 100:1 to about 1:2, such as from about 20:1 to about 1:1, such as from about 8:1 to about 2:1. As used herein, the weight ratios and weight percentages refer to the total amount of organic sulfonic acids present and the total amount of peroxide adjuvants present.

The antimicrobial composition may also contain a liquid carrier. The liquid carrier can be a solubilizer for one of the components in the composition. The liquid carrier may comprise water, an alcohol, or mixtures thereof. Alcoholic solvents that may be used include ethanol, propanol, isopropanol, n-butanol, benzyl alcohol, ethylene glycol, propylene glycol, butylene glycol, or mixtures thereof and the like. The amount of liquid carrier present in the composition can be adjusted in order to adjust the hydrogen peroxide levels in the composition. The liquid carrier may be present in an amount from about 20% to about 95% by weight, such as from about 50% to about 92% by weight. For instance, one or more liquid carriers can be present in the antimicrobial composition in an amount greater than about 60% by weight, such as in an amount greater than about 70% by weight, such as in an amount greater than about 80% by weight, such as in an amount greater than about 85% by weight, such as in an amount greater than about 90% by weight and generally in an amount less than about 95% by weight.

The solubility and compatibility of the liquid antimicrobial composition can be further improved by adding suitable amounts of other solubilizers, such as a hydrotrope, surfactants, or mixtures thereof, to improve the solubility and physical properties of the solution.

Examples of hydrotrope agents include n-octanesulfonate, a xylene sulfonate, a naphthalene sulfonate, or mixtures thereof. Suitable surfactants may be selected from the group of ionic, nonionic and amphoteric surfactants, and preferably nonionic and/or ionic surfactants or mixtures thereof. Compatible nonionic surfactants include alkoxylated alcohols such as ethoxylated alcohols, alkoxylated glycols such as alkoxylated ethylene glycol or propylene glycol with a $C_6$ to $C_{18}$ alkyl group, alkylated glycols, or mixtures thereof. Ionic surfactants that may be used include alkyl sulfate, alkylethersulfate, and their alkylsulfonic acid, alkylether sulfonic acid, alkylbenzenesulfate, and their corresponding sulfonic acid. Other surfactants that may be used include a quaternary ammonium salt, or a tertiary amine N-oxide. Each of the above mentioned surfactants may be used alone or in combination with other surfactants.

When present, one or more hydrotropes may be included in the antimicrobial composition in an amount from about 0.1% to about 10% by weight, such as from about 0.2% to about 2% by weight. One or more surfactants may be present in the composition in an amount from about 0.005% to about 12% by weight, such as from about 0.2% to about 7% by weight.

In one embodiment, the antimicrobial composition of the present disclosure may further comprise a stabilizer. The stabilizer may be added to prevent the components from decomposing prematurely during storage of the concentrate and/or prior to contact with a surface or microorganism. The stabilizer may be for stabilizing the hydrogen peroxide. Examples of suitable stabilizers include acids containing phosphorus, polycarboxylic acids, and phosphates. In one embodiment, the stabilizer may comprise phosphoric acid, or a derivative of phosphoric acid. The stabilizer may also comprise a metal chelator. Examples of stabilizers include phosphoric acid, 1-hydroxyethylidenediphosphonic acid (HEDP), phytic acid, aminophosphate, phosphonate and sodium glutamate, ethylenediam ine-N,N'-disuccinic acid, $NaH_2PO_4$, Na tripolyphosphate, organophosphonic acid, amino-phosphonate, silver dihydrogen citrate, diphosphonic acid, ethylenediaminetetraacetic acid (EDTA), N-(hydroxyethyl)-ethylenediaminetriacetic acid (HEDTA), tri(methylene phosphoric acid), diethylenetriamine-penta(methylene phosphoric acid), 2-hydroxy ethylimino bis(ethylene phosphoric acid), citric acid, nitriotriacetic acid (NTA), 2-hydroxyethylimino-diacetic acid (HEIDA), and salts thereof, cyclohexane-1,2-diaminotetrakismethylene phosphonic acid or water-sol, diethylenetriamine penta(methylene phosphonic acid), colloidal stannate, diethylenetriamine pentaacetic acid (DTPA), citrate, gallate, malate, malonate, oxaloacetate, oxalate, pyruvate, and succinate or mixtures thereof.

The stabilizer can be a single component or a mixture of the derivatives of phosphoric acid and chelators described above. The amount of the stabilizer can be from about 0.01% to about 10%, preferably from about 0.05% to about 5%, and more preferably from about 0.1% to about 1.0% by weight.

Other additives may be also added to the antimicrobial composition of the present disclosure to provide the composition with suitable properties for end use applications. Typical examples include corrosion inhibitors, emulsifiers, fragrances, dyes, preservatives, antifoam agents and mixtures thereof.

In one embodiment, for instance, the antimicrobial composition may contain a corrosion inhibitor. Corrosion inhibitors that may be used include borates, phosphates, polyphosphates, sodium benzoate, sodium gluconate, sodium silicate, sodium molybdate, sodium bisulfate, benzotriazole or mixtures thereof. When present, the corrosion inhibitor can be contained in the composition in an amount from about 0.001% to about 10% by weight, such as from about 0.01% to about 1% by weight.

In order to produce an antimicrobial composition in accordance with the present disclosure, the different ingredients can be added together to form a liquid medium. In general, the ingredients and components used to make the antimicrobial composition can be mixed in any suitable order. In one aspect, however, the hydrogen peroxide source may be added last to the remainder of the components.

In one aspect, the peroxide adjuvant can first be mixed with water. The organic sulfonic acid can then be added followed by the hydrogen peroxide. If desired, a stabilizer can then be added followed by adding amounts of sodium hydroxide to reach a desired pH level.

In one embodiment, a relatively concentrated antimicrobial composition is produced and sold or otherwise distributed to end users. An end user can then dilute the concentrated solution during or prior to use. Of particular advantage, the antimicrobial composition can be diluted with water, such as tap water.

In one embodiment, a relatively concentrated antimicrobial composition is produced that contains hydrogen peroxide in an amount from about 15% to about 60% by weight, such as from about 30% to about 55% by weight, one or more organic sulfonic acids in an amount of from about 5% to about 35% by weight, such as from about 15% to about 30% by weight, and one or more peroxide adjuvants in an amount of from about 2% to about 12% by weight, such as an amount from about 4% to about 10% by weight. In one aspect, the concentrated antimicrobial composition may contain hydrogen peroxide in an amount of from about 35% to about 50% by weight, an organic sulfonic acid in an amount of from about 22% to about 27% by weight, a peroxide adjuvant in an amount from about 4% to about 8% by weight, and water in an amount from about 15% to about 22% by weight. Other ingredients may be present, which may reduce the water content.

In still another aspect, an antimicrobial composition precursor can be formulated that can then be combined later with a peroxide source. The peroxide source, for instance, can be added to the composition at the point of application. In this manner, the peroxide source remains in a completely activated state. For example, the antimicrobial composition precursor can contain an organic sulfonic acid combined with a peroxide adjuvant and a base, such as a metal hydroxide. The base, for instance, can be sodium hydroxide. In one aspect, the antimicrobial composition precursor can contain an organic sulfonic acid in an amount greater than about 15% by weight, such as in an amount greater than about 25% by weight, such as in an amount greater than about 35% by weight and generally in an amount less than about 60% by weight, such as in an amount less than about 50% by weight, such as in an amount less than about 45% by weight. The peroxide adjuvant can be present in the composition in an amount greater than about 5% by weight, such as in an amount greater than about 8% by weight and generally in an amount less than about 20% by weight, such as in an amount less than about 15% by weight, such as in an amount less than about 12% by weight. The composition can contain a base, such as sodium hydroxide, in an amount greater than about 3% by weight, such as in an amount greater than about 7% by weight, such as in an amount greater than about 9% by weight, and generally in an amount less than about 20% by weight, such as in an amount less than about 15% by weight, such as in an amount less than about 12% by weight. The antimicrobial composition precursor can further contain water and other additives. When ready for use, the antimicrobial composition precursor can be combined with a hydrogen peroxide source and further amounts of water in order to be within the antimicrobial formulations described above.

In general, the antimicrobial composition has a neutral to acidic pH. The pH of the composition, for instance, can be from about 2 to about 6, such as from about 1 to about 4, such as from about 1.25 to about 3.

The antimicrobial composition may be used in any suitable application where disinfecting, sanitizing, cleaning and/or bleaching are desired. The antimicrobial composition can be used for consumer household use, for use in the healthcare field, for use in the food processing field or food service field, for use in sterilizing surfaces in dairies and breweries, for use in the veterinarian field, and/or for use in clean rooms.

The antimicrobial composition can be applied to an opposing surface using various methods and techniques. For instance, the antimicrobial composition can be sprayed onto the opposing surface or an object can be dipped into the composition.

One particularly useful application method is to impregnate the antimicrobial composition into a wipe substrate. The wipe can be a single use wipe that is impregnated with the antimicrobial composition and is stored in a container that will dispense the wipe to a user. The container with the wipes may contain a single wipe, or several wipes. Suitable containers include a pouch containing a single wipe, such as a moist towelette which is torn open by the user, or may be a pouch or other container with a resealable opening containing several wipes in a stacked fashion, a rolled fashion or other suitable formation that would allow a single wipe to be removed from the opening at a time. Pouches are generally prepared form a fluid impervious material, such as a film, a coated paper or foil or other similar fluid impervious materials. In another way to dispense wipes of the present disclosure is to place the wipe in to a fluid impervious container having an opening to access the wipes in the container. Containers may be molded plastic container with lids that are fluid impervious. Generally, the lid will have an opening to access the wipes in the container. The wipe in the container may be in an interleaved stack, such that as a wipe is removed from the container, the next wipe is positioned in the opening of the container ready for the user to remove the next wipe. Alternatively, the wipe may be a continuous material which is perforated between the individual wipes of the continuous material. The continuous wipe material with perforations may be in a folded form or may be in a rolled form. Usually, in the rolled form, the wipe material is fed from the center of the rolled material. As with the interleaved stack, as a wipe is removed from the container, the next wipe is positioned in the opening to facilitate removal of the next wipe, when needed.

The antimicrobial composition can be impregnated into the wipe such that the wipe is pre-moistened and will express or release the antimicrobial composition onto the surface as the wipe is run across the surface to be treated. Generally, the antimicrobial composition is saturated into the wipe such that the wipe will release the antimicrobial composition to the surface through the wiping action. Generally, the antimicrobial composition is present in an amount of from about 2 parts to 6 parts by weight per 1 part by weight of the wiper substrate, more preferably from about 3 to about 5 parts by weight per 1 part by weight of the wiper substrate. In these ranges, complete saturation of the substrates can be achieved. It is noted that the amount of the antimicrobial composition may go up or down to achieve complete saturation of the wipe substrate, depending on the particular wipe substrate.

Suitable wipe substrates include woven and nonwoven materials. Essentially any nonwoven web material may be used. Exemplary nonwoven materials may include, but are not limited to meltblown, coform, spunbond, airlaid, hydroentangled nonwovens, spunlace, bonded carded webs, and laminates thereof. Optionally, the nonwoven may be laminated with a film material as well. The fibers used to prepare the wipe substrate may be cellulosic fiber, thermoplastic fibers and mixtures thereof. The fibers may also be continuous fibers, discontinuous fibers, staple fibers and mixtures thereof. Basis weights of the nonwoven web may vary from about 12 grams per square meter to 200 grams per square meter or more.

Once applied to the surface, the antimicrobial composition is allowed to remain on the surface for a period of time. As mentioned, it has been unexpectedly found that the described antimicrobial composition has dramatically reduced contact times necessary for killing the targeted microorganisms.

Figure 2:
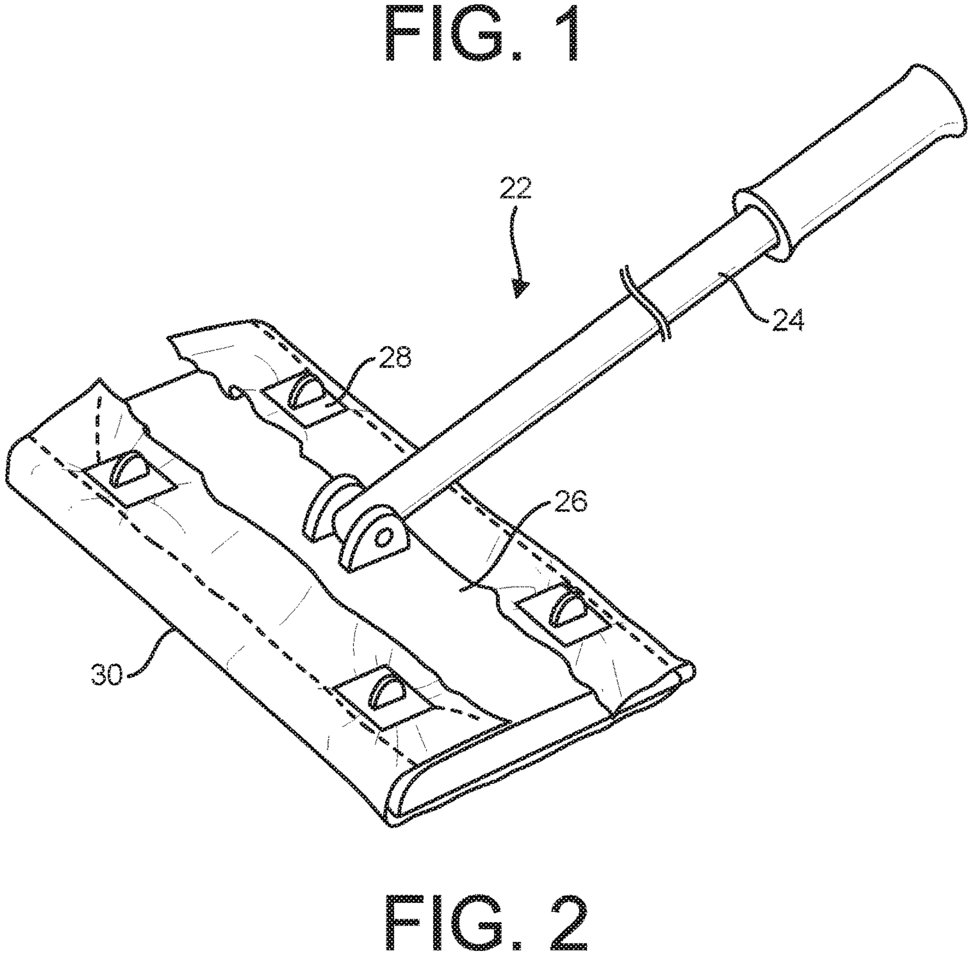
FIG. 2 is a perspective view of another embodiment of a wiping product made in accordance with the present disclosure.

Referring to FIGS. 1 and 2, exemplary embodiments of wiping products made in accordance with the present disclosure are illustrated. Referring to FIG. 1, for instance, a wiping product 10 is illustrated. The wiping product 10 includes a dispenser 12. The dispenser 12 includes a bottom 14 and a top 16. The top 16 defines an opening or slot 18 through which premoistened wipes are dispensed. The premoistened wipes can be contained in the dispenser 12 as a single roll of material or can be stacked as individual wipes. The wipes 20 are for disinfecting any suitable hard surface and can be presaturated or premoistened with the antimicrobial composition of the present disclosure as described above.

Referring to FIG. 2, an alternative embodiment of a wiping product 22 is illustrated. The wiping product 22 as shown in FIG. 2 is particularly well suited for cleaning floors. As described above, for instance, the antimicrobial composition of the present disclosure can be formulated for application to floors without harming or adversely interfering with a floor coating or floor finish.

As shown in FIG. 2, the wiping product 22 includes a handle 24 attached to a substrate holder 26. The substrate holder 26 includes a plurality of attachment devices 28 that are designed to engage and attach to a premoistened wipe 30. The premoistened wipe 30 includes a liquid absorbent substrate that has been saturated or wetted with the antimicrobial composition of the present disclosure.

The present disclosure may be better understood with reference to the following examples.

EXAMPLES

The following examples demonstrate some of the advantages and benefits of the present disclosure.

Various different antimicrobial formulations were produced and tested against *Clostridium difficile*. The following test procedures were used.

ASTM Standard E2197-11. Standard Quantitative Disk Carrier Test Method (QCT-2) for Determining Bactericidal, Virucidal, Fungicidal, Mycobactericidal and Sporicidal Activities of Chemicals.

ASTM E2839-11. Standard Test Method for Production of *Clostridium difficile* Spores for Use in Efficacy Evaluation of Antimicrobial Agents.

Office of Pesticides Programs Microbiology Laboratory Environmental Science Center, Ft. Meade, MD. SOP Number: MB-31.01 Date Revised: Feb. 2, 2005-2014.

In a first set of experiments, two different antimicrobial compositions were formulated and tested. Sample No. 1 was made in accordance with the present disclosure containing both an organic sulfonic acid and a peroxide adjuvant. The following results were obtained.

TABLE 1

| Ingredients | Sample No. 1 % w/w | Sample No. 2 % w/w |
|---|---|---|
| Water | 85.85 | 86.47 |
| H2O2(50%) | 8.00 | 8.00 |
| Methanesulfonic Acid (70%) | 4.00 | 4.00 |
| Sodium Formate | 1.16 | — |
| Formic Acid | 0.46 | — |
| Na-Methanesulfonic Acid (99%) | — | 1.00 |
| Sodium Citrate dihydrate | — | — |
| Citric acid Anhydrous | — | — |
| Dequest 2010LC HEDP** | 0.53 | 0.53 |
| Total | 100.00 | 100.00 |
| C.diff Micro-efficacy Test at 3 min contact time | | |
| $Log_{10}$ Reduction | 6.13 | <1.36 |

**1.Hydroxyethylidene.1,1.diphosphonic acid

The above liquid formulations were evaluated for efficacy against *Clostridium difficile* (*C. difficile*) spores at 3 minute contact time using the ASTM Quantitative Carrier test Method (ASTM E2197-11 and ASTM E2839-11).

As shown above, Sample No. 1 made in accordance with the present disclosure performed dramatically and unexpectedly better than Sample No. 2 when tested against *C. difficile*.

Four more antimicrobial compositions were then formulated and tested as indicated in the Table below.

TABLE 2

| Ingredients | Sample No. 3 % w/w | Sample No. 4 % w/w | Sample No. 5 % w/w | Sample No. 6 % w/w |
|---|---|---|---|---|
| Water | 87.47 | 87.85 | 85.85 | 85.82 |
| H2O2(50%) | 8 | 8 | 8.00 | 8.00 |
| Methanesulfonic Acid (70%) | 4 | — | 4.00 | 2.03 |
| Sodium Formate | | 1.16 | 1.16 | 1.16 |
| Formic Acid | — | 2.46 | 0.46 | 1.46 |
| Na-Glycolate (97%) | — | — | — | — |
| Glycolic acid (70%) | — | — | — | 1.00 |
| Dequest 2010LC HEDP** | 0.53 | 0.53 | 0.53 | 0.53 |
| Total | 100 | 100 | 100 | 100 |
| C.diff Micro-efficacy Test at 3 min contact time | | | | |
| $Log_{10}$ Reduction | <1.33 | 3.13 | 6.13 | 6.45 |

**1.Hydroxyethylidene.1,1.diphosphonic acid

As shown above, Sample Nos. 5 and 6 containing both an organic sulfonic acid and formic acid were efficacious against *C. difficile*. In Sample No. 6, glycolic acid was also present which enhanced the efficacy of the composition.

Four more antimicrobial formulations were formulated in accordance with the present disclosure. The amount of sodium formate and formic acid was varied in each sample. The following results were obtained.

TABLE 3

| Ingredients | Sample No. 7 % w/w | Sample No. 8 % w/w | Sample No. 9 % w/w | Sample No. 10 % w/w |
|---|---|---|---|---|
| Water | 85.85 | 85.85 | 85.85 | 85.85 |
| H2O2(50%) | 8.00 | 8.00 | 8.00 | 8.00 |
| Methanesulfonic Acid (70%) | 4.00 | 4.00 | 4.00 | 4.00 |
| Sodium Formate | 1.16 | 1.30 | 1.40 | — |
| Formic Acid | 0.46 | 0.32 | 0.22 | 1.00 |
| Dequest 2010LC HEDP** | 0.53 | 0.53 | 0.53 | 0.53 |
| Total | 100 | 100 | 100 | 100 |
| C.diff Micro-efficacy Test at 3 min contact time | | | | |
| $Log_{10}$ Reduction | 6.13 | 6.03 | 6.33 | 6.3 |

Three more antimicrobial formulations were formulated in accordance with the present disclosure. The amount of total free formic acid in the formulations was varied.

TABLE 4

| Ingredients | Sample No. 12 | Sample No. 13 | Sample No. 14 |
|---|---|---|---|
| Water | q.s. to 100 | q.s. to 100 | q.s. to 100 |
| Total formic Acid | 0.90 | 0.95 | 1.00 |
| H2O2 (50%) | 8.00 | 8.00 | 8.00 |
| MSA (70%) | 4.00 | 4.00 | 4.00 |
| HEDP** | 0.53 | 0.53 | 0.53 |
| C.diff Log10 Reduction at 3 min. contact time | 6.21 | 6.21 | 6.21 |

As shown above, all of the formulations (containing 0.9% total formic acid or greater) where sufficient to enhance the efficacy of hydrogen peroxide against *C. difficile.*

Three more antimicrobial formulations were formulated. The pH of the formulations were adjusted to determine its effects.

TABLE 6

| Ingredients | Sample 15 | Sample 16 | Sample 17 |
|---|---|---|---|
| Water | 78.60 | 85.36 | 78.39 |
| Formic Acid | 0.95 | 1.00 | 1.00 |
| H2O2 (27%) | 14.81 | — | 14.81 |
| H2O2 (50%) | — | 8.00 | — |
| MSA (70%) | 4.00 | 4.00 | 4.00 |
| NaOH | 1.11 | 1.11 | 1.27 |
| HEDP** | 0.53 | 0.53 | 0.53 |
| Total | 100.00 | 100.00 | 100.00 |
| Total Free Formic Acid | 0.95 | 1.00 | 1.00 |
| C. diff (3 min) Log10 Reduction | 6.09 | 6.21 | 5.26 |
| pH | 1.44 | 1.5 | 2.17 |

Sodium hydroxide was used to adjust the pH of the formulations above. As shown above, a pH range of from about 1 to about 3 show great efficacy against *C. difficile.*

The following is an example of a concentrated formulation that can later be diluted with water and used as an antimicrobial composition.

TABLE 7

Example of the concentrated formulation

| Ingredients | Sample No. 15 % w/w |
|---|---|
| Water | 18.82 |
| H2O2(50%) | 48.00 |

TABLE 7-continued

Example of the concentrated formulation

| Ingredients | Sample No. 15 % w/w |
|---|---|
| Methanesulfonic Acid (70%) | 24.00 |
| Formic Acid | 6.00 |
| Dequest 2010LC HEDP** | 3.18 |

In one aspect, an antimicrobial composition precursor can be formulated that can later be combined with a hydrogen peroxide source. The following is an example of an antimicrobial composition precursor.

TABLE 8

| Ingredients | Sample No. 16 % w/w |
|---|---|
| Water | 33.70 |
| Sodium hydroxide | 11.0 |
| Methanesulfonic Acid (70%) | 40.00 |
| Formic Acid | 10.00 |
| Dequest 2010LC HEDP** | 5.30 |

The above antimicrobial composition precursor can be formulated into an antimicrobial composition, for example, using the following formulations:

TABLE 9

| Ingredients | Sample No. 17 % w/w | Sample No. 18 % w/w |
|---|---|---|
| Water | 82.00 | 75.19 |
| Sample No. 16 | 10.00 | 10.00 |
| Hydrogen peroxide (50%) | 8.00 | — |
| Hydrogen peroxide (27%) | — | 14.81 |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An antimicrobial composition comprising:

hydrogen peroxide; and a peroxide adjuvant, the peroxide adjuvant comprising formic acid, a formic acid salt, or mixtures thereof, wherein the antimicrobial composition is free of acetic acid, peracetic acid, or chlorine bleach;

wherein the hydrogen peroxide and the peroxide adjuvant are present in the composition in a weight ratio of from 8:1 to 2:1;

wherein the antimicrobial composition further comprises an organic sulfonic acid; wherein the organic sulfonic acid comprises a C1-C5 alkylsulfonic acid, a sulfonated C1-C5 carboxylic acid, a substituted or unsubstituted aromatic sulfonic acid, mono-alkylphenylsulfonic acid, a di-alkylphenylsulfonic acid, or mixtures thereof, and wherein the substituted aromatic sulfonic acid, if present, is substituted with at least one C1-C3 alkyl group and wherein the hydrogen peroxide and the organic sulfonic acid are present in the composition in a weight ratio of from 3:1 to 1:0.9.

2. The antimicrobial composition as defined in claim 1, wherein the organic sulfonic acid comprises methane sulfonic acid, benzene sulfonic acid, toluene sulfonic acid, xylene sulfonic acid, ethylbenzene sulfonic acid, or mixtures thereof.

3. The antimicrobial composition as defined in claim 1, wherein the hydrogen peroxide is present in the composition in an amount from about 0.2% to about 20% by weight, the peroxide adjuvant is present in the composition in an amount from about 0.05% to about 7% by weight, and/or the organic sulfonic acid is present in the composition in an amount of from about 0.1% to about 8% by weight.

4. The antimicrobial composition as defined in claim 1, wherein the composition has a pH of from about 1 to about 5.

5. The antimicrobial composition as defined in claim 1, further containing a liquid carrier, the liquid carrier comprising water, an alcohol, or mixtures thereof.

6. The antimicrobial composition as defined in claim 1, wherein the composition achieves at least a 4 log 10 reduction after a 3 minute contact time when tested against *C. difficile* according to ASTM Test Methods E2197-11 and E2839-11.

7. A wiping product comprising:

a liquid absorbent substrate; and an antimicrobial composition as defined in claim 1, the antimicrobial composition being absorbed into the substrate.

8. A method for disinfecting a hard surface comprising:

contacting a surface with an antimicrobial composition as defined in claim 1.

9. The method as defined in claim 8, wherein the hard surface comprises a surface used in the health care industry or in the veterinarian industry, and/or wherein the hard surface comprises food processing equipment or a food preparation surface.

10. The method as defined in claim 8, wherein the antimicrobial composition is applied to a liquid absorbent substrate and then contacted with the surface using the substrate.

* * * * *